United States Patent
Kassab et al.

(10) Patent No.: US 10,702,387 B2
(45) Date of Patent: Jul. 7, 2020

(54) DEVICES AND METHODS FOR CONTROLLING BLOOD PERFUSION PRESSURE ALONG WITH REGIONAL MILD HYPOTHERMIA

(71) Applicant: CVDevices, LLC, San Diego, CA (US)

(72) Inventors: Ghassan S. Kassab, La Jolla, CA (US); Jose A. Navia, Sr., Buenos Aires (AR)

(73) Assignee: CVDevices, LLC, San Diego, CA (US)

( * ) Notice: Subject to any disclaimer, the term of this patent is extended or adjusted under 35 U.S.C. 154(b) by 206 days.

(21) Appl. No.: 15/620,359

(22) Filed: Jun. 12, 2017

(65) Prior Publication Data

US 2017/0273791 A1    Sep. 28, 2017

Related U.S. Application Data

(63) Continuation of application No. 13/965,548, filed on Aug. 13, 2013, now Pat. No. 9,675,458, which is a
(Continued)

(51) Int. Cl.
*A61F 2/24* (2006.01)
*A61M 1/36* (2006.01)
(Continued)

(52) U.S. Cl.
CPC ........ *A61F 2/2493* (2013.01); *A61B 17/1204* (2013.01); *A61B 17/12036* (2013.01);
(Continued)

(58) Field of Classification Search
CPC .. A61F 2210/0004; A61F 2/07; A61F 2/2493; A61M 1/3613; A61M 1/3659;
(Continued)

(56) References Cited

U.S. PATENT DOCUMENTS

| 4,459,977 A | 7/1984 | Pizon et al. |
| 4,850,969 A | 7/1989 | Jackson |

(Continued)

FOREIGN PATENT DOCUMENTS

| WO | 2006/031597 | 3/2006 |
| WO | 2006/058290 | 6/2006 |
| WO | WO 2011/097295 | * 8/2011 |

OTHER PUBLICATIONS

International Searching Authority, International Search Report, dated Mar. 1, 2007, PCT/US2006/029223.
(Continued)

*Primary Examiner* — Thomas McEvoy
(74) *Attorney, Agent, or Firm* — Reichel Stohry Dean LLP; Mark C. Reichel; Natalie J. Dean

(57) ABSTRACT

Methods and devices for controlling blood perfusion pressure along with regional mild hypothermia. In at least one embodiment of a device for controlling blood perfusion pressure within a vessel of the present disclosure, the device comprises an elongated body having a lumen, a proximal end configured for placement in a first area having a first blood pressure, and a distal end configured for placement in a second area having a second blood pressure, a partial occluder positioned within the lumen of the elongated body between the proximal end and the distal end, the partial occluder configured so not to fully occlude a blood vessel and to equalize the first blood pressure at the first area with the second blood pressure at the second area, and a regional hypothermia system operably coupled thereto, the regional hypothermia system operable to reduce and/or regulate a temperature of a bodily fluid flowing therethrough.

20 Claims, 7 Drawing Sheets

Related U.S. Application Data continuation-in-part of application No. 13/562,602, filed on Jul. 31, 2012, now Pat. No. 9,132,010, which is a continuation of application No. 11/997,139, filed as application No. PCT/US2006/029223 on Jul. 28, 2006, now Pat. No. 8,231,646.

(60) Provisional application No. 61/682,345, filed on Aug. 13, 2012, provisional application No. 60/703,422, filed on Jul. 29, 2005.

(51) Int. Cl.
| | | |
|---|---|---|
| *A61F 2/07* | (2013.01) | |
| *A61B 17/12* | (2006.01) | |
| *A61M 25/04* | (2006.01) | |
| *A61F 7/12* | (2006.01) | |
| *A61F 2/06* | (2013.01) | |
| *A61F 7/00* | (2006.01) | |
| *A61M 25/00* | (2006.01) | |
| *A61M 25/10* | (2013.01) | |

(52) U.S. Cl.
CPC .......... *A61B 17/12109* (2013.01); *A61F 2/07* (2013.01); *A61F 7/12* (2013.01); *A61M 1/3613* (2014.02); *A61M 25/04* (2013.01); *A61F 2/06* (2013.01); *A61F 2007/0056* (2013.01); *A61F 2210/0004* (2013.01); *A61F 2250/0003* (2013.01); *A61M 25/0075* (2013.01); *A61M 2025/1052* (2013.01); *A61M 2025/1095* (2013.01)

(58) Field of Classification Search
CPC ...... A61M 1/3607; A61M 1/369; A61M 5/44; A61M 5/445
See application file for complete search history.

(56) References Cited

U.S. PATENT DOCUMENTS

| | | |
|---|---|---|
| 4,917,667 A | 4/1990 | Jackson |
| 4,927,412 A | 5/1990 | Menasche |
| 5,533,957 A | 7/1996 | Aldea |
| 5,655,548 A | 8/1997 | Nelson et al. |
| 5,833,662 A | 11/1998 | Stevens |
| 5,908,407 A | 6/1999 | Frazee et al. |
| 6,045,531 A | 4/2000 | Davis |
| 6,186,972 B1 | 2/2001 | Nelson et al. |
| 6,228,111 B1 | 5/2001 | Tormala et al. |
| 6,368,346 B1 | 4/2002 | Jadhav |
| 6,447,539 B1 | 9/2002 | Nelson et al. |
| 6,500,145 B1 | 12/2002 | Bicakci et al. |
| 6,613,037 B2 | 9/2003 | Khosravi et al. |
| 6,926,689 B2 | 8/2005 | Scheule |
| 7,004,925 B2 | 2/2006 | Navia et al. |
| 7,004,926 B2 | 2/2006 | Navia et al. |
| 7,473,237 B2 | 1/2009 | Navia et al. |
| 7,819,856 B2 | 10/2010 | Bates |
| 8,231,646 B2 | 7/2012 | Kassab |
| 9,132,010 B2 | 9/2015 | Kassab |
| 2002/0077581 A1 | 6/2002 | Davidner et al. |
| 2003/0065386 A1 | 4/2003 | Weadock |
| 2003/0125798 A1 | 7/2003 | Martin |
| 2003/0130668 A1 | 7/2003 | Nieman et al. |
| 2003/0181843 A1 | 9/2003 | Bibber et al. |
| 2004/0087905 A1* | 5/2004 | Breznock .............. A61M 27/00 604/164.04 |
| 2004/0172004 A1 | 9/2004 | Mohl |
| 2004/0267084 A1 | 12/2004 | Navia et al. |
| 2005/0101902 A1 | 5/2005 | Navia et al. |
| 2006/0074399 A1 | 4/2006 | Bates |
| 2006/0085028 A1 | 4/2006 | Boock |
| 2006/0184088 A1 | 8/2006 | Van Bibber et al. |
| 2006/0195060 A1 | 8/2006 | Navia et al. |
| 2007/0010781 A1 | 1/2007 | Vijay |
| 2010/0222637 A1* | 9/2010 | Kassab .............. A61B 5/02152 600/17 |
| 2013/0190682 A1 | 7/2013 | Bonutti |

OTHER PUBLICATIONS

International Searching Authority, Written Opinion of the International Searching Authority, dated Mar. 1, 2007, PCT/US2006/029223.

* cited by examiner

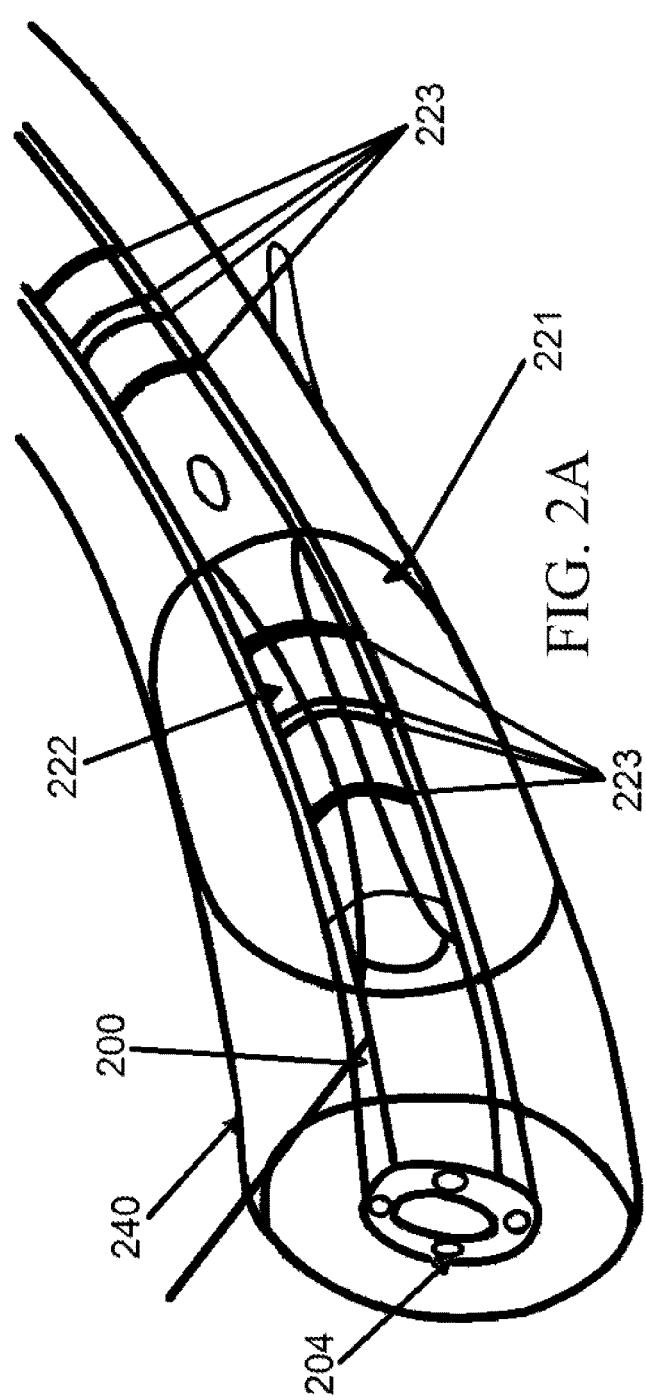
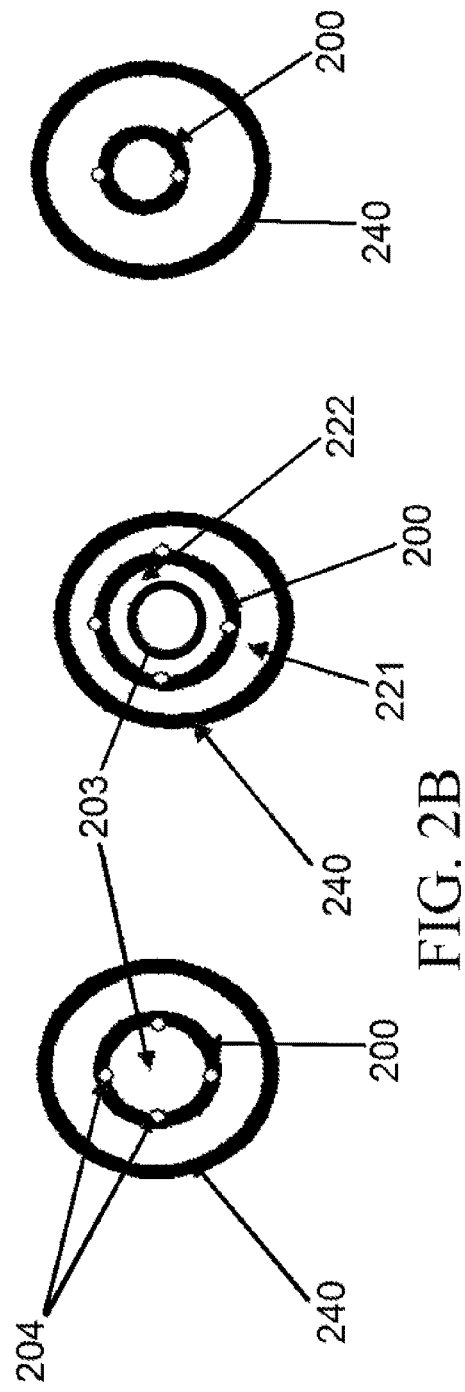
FIG. 2A
FIG. 2B

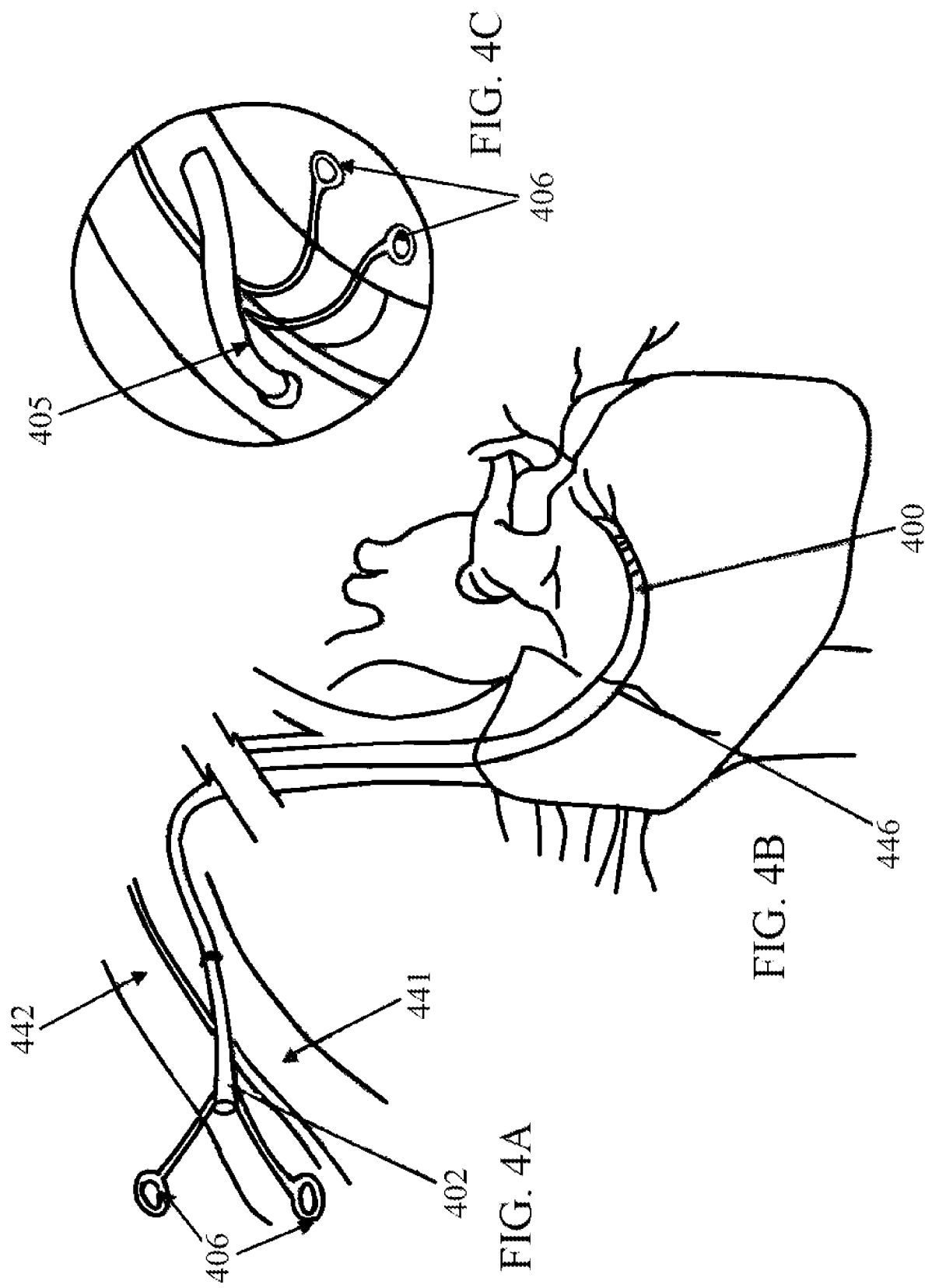

DEVICES AND METHODS FOR CONTROLLING BLOOD PERFUSION PRESSURE ALONG WITH REGIONAL MILD HYPOTHERMIA

PRIORITY

The present application is related to, claims the priority benefit of, and is a U.S. continuation patent application of, U.S. Nonprovisional patent application Ser. No. 13/965,548, filed Aug. 13, 2013, which (a) is related to, and claims the priority benefit of, U.S. Provisional Patent Application Ser. No. 61/682,345, filed Aug. 13, 2012, and (b) is related to, claims the priority benefit of, and is a continuation-in-part of, U.S. patent application Ser. No. 13/562,602, filed Jul. 31, 2012 and issued as U.S. Pat. No. 9,132,010 on Sep. 15, 2015, which is related to, claims the priority benefit of, and is a continuation application of, U.S. patent application Ser. No. 11/997,139, filed May 14, 2008 and issued as U.S. Pat. No. 8,231,646 on Jul. 31, 2012, which is related to, claims the priority benefit of, and is a § 371 national stage application of, International Patent Application Serial No. PCT/US2006/029223, filed Jul. 28, 2006, which is related to, and claims the priority benefit of, U.S. Provisional Patent Application Ser. No. 60/703,422, filed Jul. 29, 2005. The contents of each of the aforementioned applications and patent are hereby incorporated by reference in their entirety into this disclosure.

BACKGROUND

The concept of myocardial salvage through coronary sinus intervention dates back to the nineteenth century. The objective has been to increase the flow of oxygenated blood to the ischemic myocardium by perfusing the coronary bed retrogradely from the coronary sinus; i.e., coronary retroperfusion. To date, a number of retroperfusion methods have been developed. Pressure-controlled intermittent coronary sinus occlusion (PICSO) has been used in conjunction with a balloon-tipped catheter positioned just beyond the orifice of the coronary sinus with the proximal end connected to a pneumatic pump that automatically inflates and deflates the balloon according to a preset cycle. Synchronized retrograde perfusion, SRP and simplified retroperfusion are other techniques that actively pump arterial and venous blood in the former and the latter, respectively. The left ventricle-powered coronary sinus retroperfusion technique has focused on driving left ventricular blood into the coronary sinus through a surgically created left ventricle to coronary sinus shunt.

Prior studies have shown the efficacy of venous retroperfusion. It has been demonstrated that (1) coronary venous bypass-graft (CVBG) or percutaneous in situ coronary venous arterialization (PICVA) permit survival in the presence of LAD arterial ligation as compared with the uniform non-viability of just LAD arterial ligation without retroperfusion; (2) retroperfusion is effective because it perfuses all layers of the heart, including the subendocardium; and (3) considerable recovery of regional myocardial function with low regional capillary blood flows and low levels of retrograde arterial outflow provide evidence for possible oxygen delivery via the intramyocardial venous plexus.

The CVBG or PICVA procedure has a number of advantages over the conventional coronary artery bypass graft (CABG) procedure, including: (1) approximately 20% of revascularization candidates have angiographically diffuse atherosclerotic changes with poor runoff or small coronary arteries which makes arterial bypass or percutaneous coronary angioplasty (PTCA) unlikely to succeed. In those cases, CVBG may be the procedure of choice. Furthermore, the runoff for the coronary veins are significantly larger than those of arteries and hence the surgical implementation is much easier as is the improved patency of the graft. (2) The coronary venous system of the heart rarely undergoes atherosclerotic changes. This reduces the problem of restenosis that is commonly evident with the CABG procedure and should reduce the need for multiple surgeries throughout the patient's lifespan. (3) The CVBG is surgically easier to implement than the CABG procedure and does not require cardiac arrest and the use of extracorporeal circulation. The CVBG procedure can be implemented in the beating heart with the use of a cardiac restrainer. This reduces the surgical risks and ensures quicker recovery, which is particularly important in the elderly and the severely ill patients.

To emphasize the importance of this field in terms of numbers, there are about 1.4 million annual incidences of myocardial infarction in the U.S. and an equal number in Western Europe. Approximately 20% of those patients are not good candidates for bypass because of diffuse coronary artery disease. Those patients have little treatment options other than heart transplant. The number of heart transplants is meager, however, at 2,000 in 2005. Many of those patients progress to heart failure where the cost of treatment of is very high ($40 billion annually in US representing 5.4% of total health care cost). The prospect of a device to treat those patients is great in terms of lives saved as well as costs reduction associated with heart failure.

Thus, a need exists in the art for an alternative to the conventional techniques of treating heart failure using retroperfusion such that the technique should be minimally invasive, easy to use and understand, simple to implement and effective in producing desired results.

BRIEF SUMMARY

The present disclosure relates generally to controlling blood pressure, including devices and methods for controlling blood pressure using a retrograde cannula.

The present disclosure provides devices and methods for assisting in the proper retroperfusion of various organs (e.g., brain, eye, etc.) but in particular the heart. A general goal is to develop a coronary venous retroperfusion cannula that will provide perfusion of the coronary bed retrogradely through the coronary sinus with arterial blood generated from a peripheral artery with no need for a pump. The cannula will be introduced from the axillary or femoral vein under local anesthesia and the proximal end, which consists of a graft, will be anastomosed to the axillary or femoral artery, respectively. Furthermore, the cannula will initially impose a significant pressure drop (approximately 50 mmHg) due to inflation of a balloon or an obstruction (stenosis) made of resorbable material, and hence will only transmit a fraction of the arterial pressure to the venous system. The intermediate pressure can be used to arterialize the venous system for 2 to 3 weeks and can then be raised to arterial pressure by release of the stenosis.

In the case of a resorbable material, as the material resorbs over a several week period, it will reduce the pressure drop and hence transmit more of the arterial pressure to the venous system. This addresses a major problem with coronary venous retroperfusion, which is the sudden increase in pressure (venous to arterial) that results in vessel edema and hemorrhage. Here, a novel cannula is presented which provides a gradual increase in pressure to allow the venous system to arterialize. The gradual increase in pressure allows arterializations of the venous system, which prevent vessel rupture. Some of the advantages of the present disclosure include, but are not limited to: (1) design of a cannula with a stenosis that will provide the desired initial pressure drop and ensure undisturbed flow into the coronary venous system; (2) pre-arterialization of the venous system to prevent edema and hemorrhage, (3) elimination of the need for a pump as blood is delivered from the patient's artery; (4) percutaneous delivery of the system with no need for open heart surgery; and (5) delivery of cannula in the beating heart to eliminate cardiac arrest such as in bypass surgery.

Since the coronary veins do not develop arteriosclerosis, it is desirable to use these vessels as conduits for revascularization. More than 60 years ago, Roberts et al. suggested the use of coronary veins as conduits to deliver oxygenated blood in a retrograde manner in animal studies. Five years after this seminal study, Beck and colleagues performed the coronary retroperfusion procedure in humans. The method was abandoned, however, due to the high mortality rate from the edema and hemorrhage that result due to the elevated pressure. Furthermore, graft clots and atherosclerotic changes occur in the venous vessels in response to the abrupt change in pressure, which lead to progressive venous obliteration.

In order to remedy these difficulties, the present disclosure avoids increasing the pressure in the coronary vein from venous (10-20 mmHg) to arterial values (100-120 mmHg) in a single step. Instead, a cannula is presented that regulates the pressure in the venous system over time to a more gradual increase in pressure. This procedure allows the venous vessels to arterialize and the vessel walls to thicken in order to decrease the stress and prevent rupture of the post capillary venules. Furthermore, the gradual increase in pressure will decrease the injury response and subsequently reduce the atherosclerotic changes of the large epicardial veins.

In at least one exemplary embodiment of a device for controlling blood perfusion pressure within a vessel of the present disclosure, the device comprises an elongated body having a lumen, a proximal end configured for placement in a first area having a first blood pressure, and a distal end configured for placement in a second area having a second blood pressure, and a partial occluder positioned within the lumen of the elongated body between the proximal end and the distal end, the partial occluder configured so not to fully occlude a blood vessel, wherein the partial occluder is configured to equalize the first blood pressure at the first area with the second blood pressure at the second area. In another embodiment, at least one of the proximal end and the distal end is/are configured for placement within a mammalian heart. In yet another embodiment, the proximal end is configured for placement within an axillary artery or a femoral artery. In an additional embodiment, the distal end is configured for placement within an axillary vein or a femoral vein.

In at least one exemplary embodiment of a device for controlling blood perfusion pressure within a vessel of the present disclosure, the partial occluder comprises a resorbable stenosis, wherein the resorbable stenosis is configured to be resorbed over time when contacted by blood flowing from the proximal end to the distal end of the elongated body. In an additional embodiment, the resorbable stenosis is further configured to gradually equalize the first blood pressure at the first area with the second blood pressure at the second area. In yet an additional embodiment, the resorbable stenosis comprises a material selected from the group consisting of polyols and magnesium alloy.

In at least one exemplary embodiment of a device for controlling blood perfusion pressure within a vessel of the present disclosure, the partial occluder comprises an occlusion balloon, wherein the occlusion balloon is configured for inflation to partially occlude the lumen when in an inflated state and further configured for deflation or removal after a period of time. In another embodiment, the occlusion balloon is further configured to gradually equalize the first blood pressure at the first area with the second blood pressure at the second area. In yet another embodiment, the partial occluder is located closer to the proximal end than the distal end of the elongated body. In an additional embodiment, the elongated body further comprises an anchoring balloon configured to anchor the elongated body within part of a circulatory system.

In at least one embodiment of a method for conditioning a blood vessel to operate under higher blood pressures of the present disclosure, the method comprises introducing a distal end of an elongated tubular body into a blood vessel to be conditioned, the blood vessel having a first blood pressure therein and the elongated tubular body comprising an interior having a stenosis, the stenosis configured so not to fully occlude the blood vessel, introducing a proximal end of the elongated tubular body into a second blood vessel such that blood flow is received within the interior of the elongated tubular body, the second blood vessel comprising second blood pressure therein which is higher than the first blood pressure, and reducing the size of the stenosis over time such that the first blood pressure at the distal end of the elongated body is approximately the same as the second blood pressure at the proximal end. In another embodiment, the elongated tubular body introduced into the blood vessel and the second blood vessel further comprises an anchoring balloon configured to anchor the elongated tubular body within part of a circulatory system, and wherein the method further comprises the step of inflating the anchoring balloon to anchor the elongated tubular body within the blood vessel or the second blood vessel. In yet another embodiment, the stenosis comprises a balloon occlusion and the step of reducing the size of the stenosis over time comprises deflating or removing the balloon occlusion positioned within the interior of the elongated tubular body. In an additional embodiment, the stenosis comprises a resorbable stenosis and the step of reducing the size of the stenosis over time comprises deflating the gradual resorption of the stenosis within the interior of the elongated tubular body.

In at least one embodiment of a cannula for creating retrograde flow within part of a circulatory system of the present disclosure, the cannula comprises an elongated body having a lumen, a proximal end configured for placement in a first area having a first blood pressure, a distal end configured for placement in a second area having a second blood pressure, wherein the first blood pressure is higher than the second blood pressure, and a partial occluder positioned within the lumen of the elongated body between the proximal end and the distal end and closer to the proximal end than the distal end, the partial occluder selected from the group consisting of an occluder balloon and a resorbable stenosis, the partial occluder configured so not to fully occlude a blood vessel, wherein the partial occluder is configured to gradually equalize the first blood pressure at the first area with the second blood pressure at the second area. In another embodiment, the elongated body further comprises an anchoring balloon configured to anchor the elongated body within part of a circulatory system. In yet another embodiment, the partial occluder comprises the resorbable stenosis, wherein the resorbable stenosis is configured to be resorbed over time when contacted by blood flowing from the proximal end to the distal end of the elongated body. In an additional embodiment, the partial occluder comprises the occlusion balloon, wherein the occlusion balloon is configured for inflation to partially occlude the lumen when in an inflated state and further configured for deflation or removal after a period of time. In yet an additional embodiment, the proximal end is configured for placement within an axillary artery or a femoral artery, and wherein the distal end is configured for placement within an axillary vein or a femoral vein.

In various devices, methods, and/or cannulas of the present disclosure, the devices, cannulas, and/or systems comprising the same and/or components of the same, further comprise a regional hypothermia system of the present disclosure operably coupled thereto, the regional hypothermia system operable to reduce and/or regulate the temperature of a fluid flowing therethrough, such as blood, and/or operable to reduce and/or regulate the temperature of a vessel, a tissue, and/or an organ at or near the blood. In other embodiments, the regional hypothermia system comprises a heat exchanger configured to reduce and/or regulate the temperature of the fluid. In various embodiments, one or more components of the regional hypothermia system uses a cooling product to reduce and/or regulate the temperature of the fluid. In any number of embodiments, the devices and/or cannulas further comprise one or more temperature sensors coupled thereto, the one or more temperature sensors operable to detect a temperature of the blood, the vessel, the tissue, and/or the organ. In various embodiments, the devices and/or cannulas further comprise a remote module in wired or wireless communication with the one or more temperature sensors, the remote module operable to and configured to receive the detected temperature(s) and process the same to regulate, reduce, and/or increase the temperature of the blood, the vessel, the tissue, and/or the organ by way of altering the operation of the regional hypothermia system.

In at least one embodiment of a kit of the present disclosure, the kit comprises a regional hypothermia system of the present disclosure, and a device, a cannula, and/or a system comprising the same and/or components of the same. In various embodiments, the kit is useful to treat a condition of a mammalian tissue and/or organ by way of reducing blood, other fluid, tissue, and/or organ temperature and/or regulating the temperature of the same.

In at least one embodiment of a device for controlling blood perfusion pressure within a vessel (a perfusion device) of the present disclosure, the device comprises an elongated body having a lumen, a proximal end configured for placement in a first area having a first blood pressure, and a distal end configured for placement in a second area having a second blood pressure, a partial occluder positioned within the lumen of the elongated body between the proximal end and the distal end, the partial occluder configured so not to fully occlude a blood vessel and to equalize the first blood pressure at the first area with the second blood pressure at the second area, and a regional hypothermia system operably coupled thereto, the regional hypothermia system operable to reduce and/or regulate a temperature of a bodily fluid flowing therethrough. In another embodiment, the regional hypothermia system is further operable to reduce and/or regulate a temperature of a portion of a mammalian body, the portion selected from the group consisting of a vessel, a tissue, and an organ. In yet another embodiment, the regional hypothermia system comprises a heat exchanger configured to reduce and/or regulate the temperature of the bodily fluid. In an additional embodiment, one or more components of the regional hypothermia system uses a cooling product to reduce and/or regulate the temperature of the bodily fluid.

In at least one embodiment of a device for controlling blood perfusion pressure within a vessel (a perfusion device) of the present disclosure, the device further comprises one or more temperature sensors coupled to the device, the one or more temperature sensors operable to detect the temperature of the bodily fluid. In an additional embodiment, the regional hypothermia system further comprises a remote module in wired or wireless communication with the one or more temperature sensors, the remote module operable to and configured to receive the detected temperature(s) and process the same to regulate, reduce, and/or increase the temperature of the bodily fluid by way of altering an operation of the regional hypothermia system. In yet an additional embodiment, the partial occluder comprises a resorbable stenosis, wherein the resorbable stenosis is configured to be resorbed over time when contacted by blood flowing from the proximal end to the distal end of the elongated body. In another embodiment, the partial occluder comprises an occlusion balloon, wherein the occlusion balloon is configured for inflation to partially occlude the lumen when in an inflated state and further configured for deflation or removal after a period of time. In yet another embodiment, the elongated body further comprises an anchoring balloon configured to anchor the elongated body within part of a circulatory system.

In at least one embodiment of a method for conditioning a blood vessel to operate under higher blood pressures (a method) of the present disclosure, the method comprises the steps of introducing a distal end of an elongated tubular body into a blood vessel to be conditioned, the blood vessel having a first blood pressure therein and the elongated tubular body comprising an interior having a stenosis, the stenosis configured so not to fully occlude the blood vessel, introducing a proximal end of the elongated tubular body into a second blood vessel such that blood flow is received within the interior of the elongated tubular body, the second blood vessel comprising second blood pressure therein which is higher than the first blood pressure, reducing and/or regulating a temperature of blood flowing through the elongated tubular body using a regional hypothermia system operably coupled to the elongated tubular body, and reducing the size of the stenosis over time such that the first blood pressure at the distal end of the elongated body is approximately the same as the second blood pressure at the proximal end. In another embodiment, the elongated tubular body introduced into the blood vessel and the second blood vessel further comprises an anchoring balloon configured to anchor the elongated tubular body within part of a circulatory system, and wherein the method further comprises the step of inflating the anchoring balloon to anchor the elongated tubular body within the blood vessel or the second blood vessel. In yet another embodiment, the stenosis comprises a balloon occlusion and the step of reducing the size of the stenosis over time comprises deflating or removing the balloon occlusion positioned within the interior of the elongated tubular body. In an additional embodiment, the stenosis comprises a resorbable stenosis and the step of reducing the size of the stenosis over time comprises deflating the gradual resorption of the stenosis within the interior of the elongated tubular body. In yet an additional embodiment, the step of reducing and/or regulating a temperature of blood flowing through the elongated tubular body is performed to treat a cardiac condition.

In at least one embodiment of a cannula for creating retrograde flow within part of a circulatory system (a cannula) of the present disclosure, the cannula comprises an elongated body having a lumen, a proximal end configured for placement in a first area having a first blood pressure, a distal end configured for placement in a second area having a second blood pressure, wherein the first blood pressure is higher than the second blood pressure, a partial occluder positioned within the lumen of the elongated body between the proximal end and the distal end and closer to the proximal end than the distal end, the partial occluder selected from the group consisting of an occluder balloon and a resorbable stenosis, the partial occluder configured so not to fully occlude a blood vessel and to gradually equalize the first blood pressure at the first area with the second blood pressure at the second area, and a regional hypothermia system operably coupled thereto, the regional hypothermia system operable to reduce and/or regulate a temperature of a bodily fluid flowing therethrough. In another embodiment, the regional hypothermia system is further operable to reduce and/or regulate a temperature of a portion of a mammalian body, the portion selected from the group consisting of a vessel, a tissue, and an organ. In yet another embodiment, the regional hypothermia system comprises a heat exchanger configured to reduce and/or regulate the temperature of the bodily fluid. In an additional embodiment, the cannula further comprises one or more temperature sensors coupled thereto, the one or more temperature sensors operable to detect the temperature of the bodily fluid.

In at least one embodiment of a cannula for creating retrograde flow within part of a circulatory system (a cannula) of the present disclosure, the elongated body further comprises an anchoring balloon configured to anchor the elongated body within part of a circulatory system. In an additional embodiment, the partial occluder comprises the resorbable stenosis, wherein the resorbable stenosis is configured to be resorbed over time when contacted by blood flowing from the proximal end to the distal end of the elongated body. In yet an additional embodiment, the partial occluder comprises the occlusion balloon, wherein the occlusion balloon is configured for inflation to partially occlude the lumen when in an inflated state and further configured for deflation or removal after a period of time

BRIEF DESCRIPTION OF THE DRAWINGS

FIG. 2A shows a detailed version of a cannula's multi-lumen catheter with inner and outer balloons according to an exemplary embodiment of the present disclosure;

FIG. 2B shows cross-sectional views of exemplary embodiments of multiple lumens within a cannula according to exemplary embodiments of the present disclosure;

FIG. 4A shows a minimally invasive surgical insertion of a retroperfusion cannula with direct puncture of the axillary vein and catheterization into the coronary sinus according to an exemplary embodiment of the present disclosure;

FIG. 4B shows the cannula of FIG. 4A after the graft is fixed in position at the coronary sinus;

FIG. 4C shows the cannula of FIG. 4A as the axillary artery is prepared and the proximal side of the graft is anastomosed to the axillary artery;

DETAILED DESCRIPTION

The present disclosure describes a cannula for acute and chronic retroperfusion that is designed for percutaneous insertion into the coronary sinus and proximally connecting to the subclavian artery. This allows retroperfusion of oxygenated blood through the coronary venous system to decrease an acute ischemic area during an acute myocardial infarction event.

Figure 1:
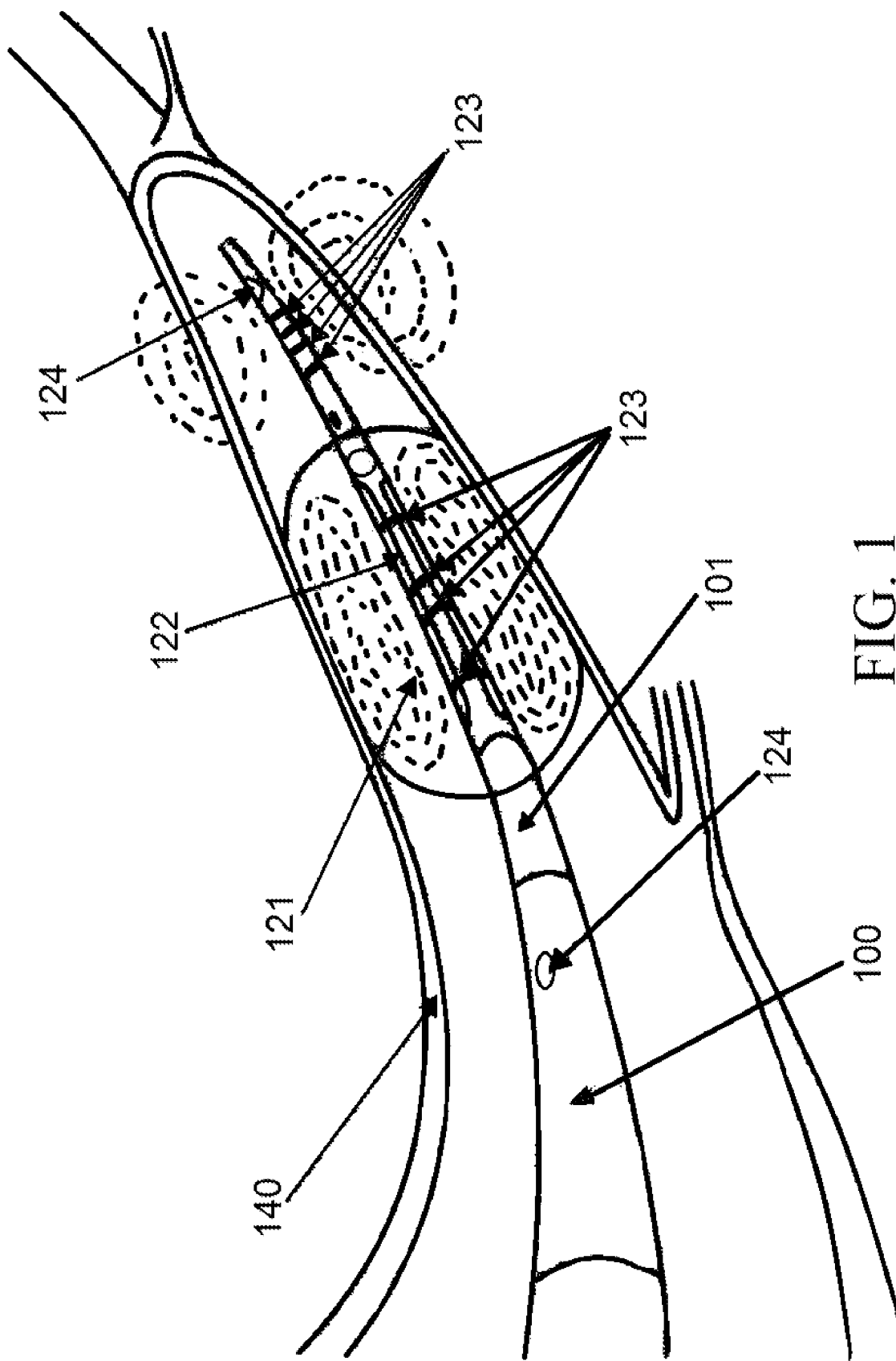
FIG. 1 shows a cannula within a vessel wall in which at a distal end, an external expandable balloon anchors the cannula in the coronary vein, while an internal balloon provides the necessary obstruction to cause a drop in pressure according to an exemplary embodiment of the present disclosure, wherein further impedance electrodes are placed distally to locally size the coronary sinus while additional electrodes are placed internal to the balloon for sufficient inflation and hence occlusion of the vein according to the distal size measurement.

An exemplary embodiment of the disclosure, illustrated in FIG. 1, shows a cannula 100 within a vessel wall 140, with the proximal portion (not shown) being a graft. The distal portion of the cannula includes a catheter 101 with an expandable external balloon 121. The catheter may be made of any appropriate material used in the art, such as polyurethane, silicone rubber, or other appropriate polymeric material. The distal end may also contain pressure sensors 124 for monitoring purposes and impedance electrodes 123 for measuring the vessel and sizing the external balloon 121 accordingly.

The external expandable balloon 121 anchors the cannula in the coronary vein. Additionally, the external balloon prevents backflow of blood leaving the cannula. In this embodiment, a second, internal balloon 122 serves to provide the pressure drop required for gradual arterialization of the vein. The balloons may be made of any material suitable for their function, including but not limited to, polyethylene, latex, polyestherurethane, or combinations thereof. The balloons may be connected to secondary lumens within the cannula, which are, in one embodiment, connected to percutaneous ports emerging from the proximal end of the cannula. The percutaneous ports may be used to inflate or deflate the balloons during retroperfusion. In one exemplary embodiment, the internal balloon 122 may be removed completely via the secondary lumen when vein arterialization is complete. As in the embodiment illustrated in FIG. 1, an external balloon and an internal balloon may be concentric to each other. In other embodiments, the internal and external balloons may be located on distinct portions of the cannula.

Some exemplary embodiments may contain two tetrapolar sets of electrodes 123 to measure the vessel near the distal tip 120 of catheter and to size the balloon accordingly. The selective region of the coronary sinus can be sized using these excitation and detection electrodes as described in more detail within the pending patent application, "System and Method for Measuring Cross-Sectional Areas and Pressure Gradients in Luminal Organs," U.S. patent application Ser. No. 10/782,149, filed on Feb. 19, 2004, which is incorporated by reference herein in its entirety. In that application, a description is provided of a conductance catheter that is used to determine size of blood vessels.

In embodiments of the cannula that do not include impedance electrodes, the sizing of the exterior balloon may also be accomplished based on the compliance of the balloon measured ex vivo and in vivo. This method requires the calibration of the balloon volume and hence diameter in vitro subsequent to in vivo. This alternative method avoids the need for electrodes and impedance sizing but may be less accurate.

Once the lumen size of the applicable region of the coronary sinus is determined, the balloon is expanded accordingly. It is recalled that a vein is rather compliant at lower pressures and hence an appropriate diameter is selected to maintain the cannula lodged into the lumen. For acute applications, saline may be used to fill the balloon. For longer term applications, gels or silicones may be used to fill the balloon.

FIG. 2A shows the distal portion of the cannula 200 within the vessel wall 240. The body of the cannula houses two or more lumens with a variety of possible configurations, some of which are shown in FIG. 2B. In the embodiment illustrated, the cannula contains a primary lumen 203 and multiple secondary lumens 204. The secondary lumens may connect to an expandable exterior balloon 221 and/or interior balloon 222. The secondary lumen may also contain pressure sensors that allow internal monitoring of the cannula during retroperfusion.

The primary lumen 203 is the conduit that allows the oxygenated blood flow derived from an artery to flow into the coronary sinus. The lumen of the catheter is designed to provide an optimal stenosis geometry for the desired initial pressure drop and to ensure undisturbed flow in the coronary venous system. In various embodiments, the secondary lumens 204 may be used for a variety of different purposes, such as inflation, deflation, and removal of interior and exterior balloons, coronary sinus pressure measurement, cannula pressure measurement, and drug delivery. In one exemplary embodiment, the secondary lumens 204 are operatively coupled with proximal extensions that branch from the graft body in such way that they are employed as percutaneous access ports.

Figure 3B:
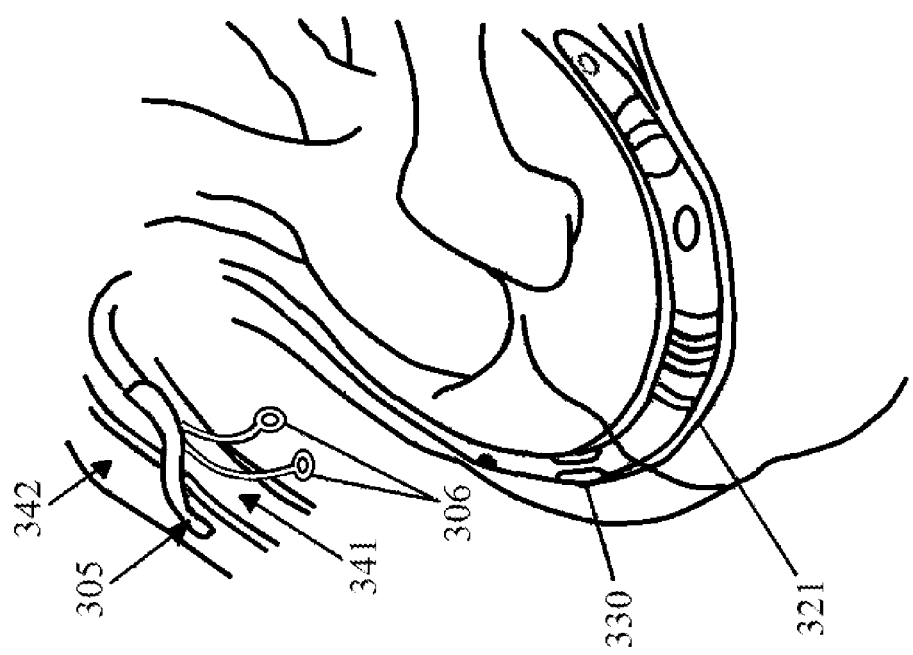
FIG. 3B shows an embodiment of a cannula containing a resorbable stenosis according to an exemplary embodiment of the present disclosure.
Figure 3A:
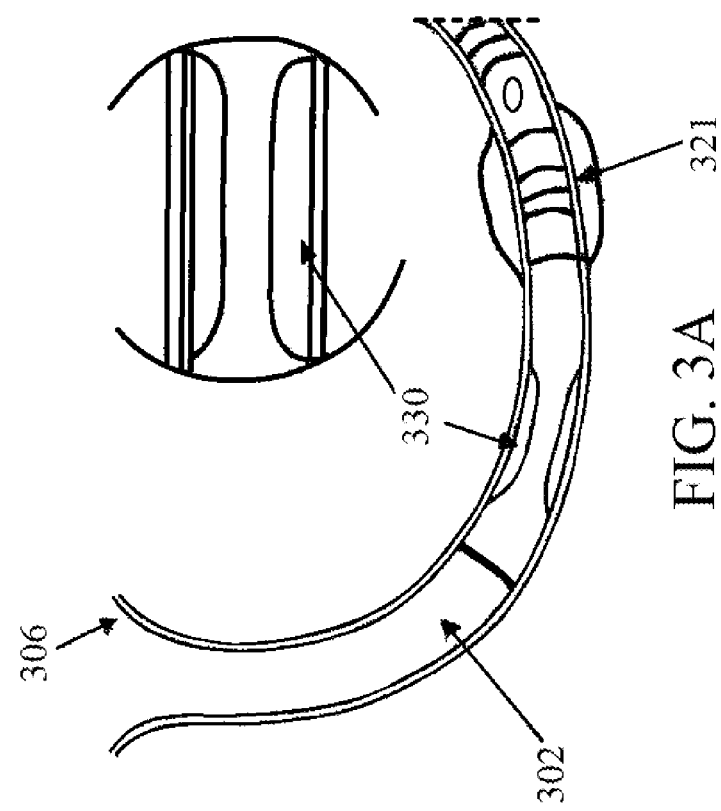
FIG. 3A shows a cannula inserted into the coronary sinus via the axillary vein according to an exemplary embodiment of the present disclosure.

FIG. 3A presents a detailed illustration of an exemplary embodiment of a cannula, with its proximal end being a graft 302, that contains a stenosis which causes a drop in the pressure of blood passing through the cannula. The stenosis can be imposed by inflation of a balloon that partially occludes the lumen or by imposing a resorbable material within the lumen. A variety of materials may be used to construct the resorbable stenosis, such as, for example, polyols and magnesium alloy. The most widely used polyols are mannitol, sorbitol and maltitol. Mannitol is used in the description of the examples herein. A mold of the computed shape will be used to construct the stenosis using computer-assisted design while the magnesium alloy geometry will be sculpted by laser from a single tube. Mannitol is a naturally occurring nonreducing acyclic sugar compound widely used in foods, pharmaceuticals, medicine and chemical industries. Crystalline Mannitol exhibits a very low hygroscopicity, making it useful in products that are stable at high humidity.

Mannitol is often added in dried protein formulations as the bulking agent as it has the tendency to crystallize rapidly from aqueous solutions. It has recently been shown that acetylsalicylic acid, which is an active ingredient of aspirin, can be mixed with Mannitol without affecting its properties. This is ideal as it will provide antithrombotic properties to prevent coagulation of blood during the resorption of the stenosis. Alternatively, magnesium alloys may be used which are currently used in drug-eluting bioabsorbable stents. Magnesium is a natural body component with beneficial antithrombotic, antiarrythmic and antiproliferative properties. The degradation rate of magnesium alloy has been shown to be linear and complete after 2-3 months. The use of degradable magnesium alloys leads to electronegative and therefore, hypothrombogenic surfaces. As an essential element, slowly degrading magnesium should not harm tissue, particularly since magnesium solutions up to 0.5 mol/l are well tolerated if given parenterally. The mechanical properties and corrosion of magnesium alloys are quite controllable under physiological conditions and match the requirements for degradable stenosis. The stenosis mold 330 is then inserted into the catheter portion of the cannula very close to the proximal inlet. The graft 302 may then be glued at this junction as shown in FIG. 3A.

It should be noted that the resorption rate of mannitol is a function of molecular weight, crystallinity, and particle size. The compound is prepared so that it will resorb in approximately 8 weeks. The magnesium alloys have been shown to resorb within 8-12 weeks.

For balloon occlusions, the desired occlusion is obtained by measurement of pressure at the tip of the cannula during inflation of the balloon. Once the desired intermediate pressure is obtained, the balloon volume is finalized. The patient is allowed to arterialize at the pressure for some time. At the end of such period (typically 2-3 weeks), the occlusion is removed by deflation of the balloon. In an exemplary embodiment, the inner lumen containing the inner balloon may be removable and hence withdrawn.

The cannula is intended for insertion from either the axillary 341 or femoral (not shown) veins into the coronary sinus. The proximal graft 302 is anastomosed to the adjacent artery 342. The graft may be made of any biocompatible, nonresorbable polymer with the necessary strength to support the surrounding tissue and withstand pressure from blood flow and the necessary flexibility to form an anastomosis with between the artery and the vein within which the cannula is housed. For example, a material such as GORE-TEX (polytetraflouroethylene) is suitable for use in the graft. In exemplary embodiments, the total length of the graft is approximately 6 cm and that of the attached catheter is 8-10 cm, but they may be of any lengths such that their dimensions allow an anastomosis between the human coronary sinus and the subclavian artery to be made. Access ports 306 which connect to and are in fluid contact with the secondary lumens branch off of the proximal graft 302 in some embodiments.

The diameter within the cannula will, in certain exemplary embodiments, be approximately 4 mm, but may be of any diameter such that the cannula allows sufficient blood flow and can be accommodated by the relevant vessels. The geometry of the stenosis will be varied to ensure an approximately 50 mm Hg pressure drop and a sufficient entrance length into the coronary vein to ensure fully developed flow.

Figure 5B:
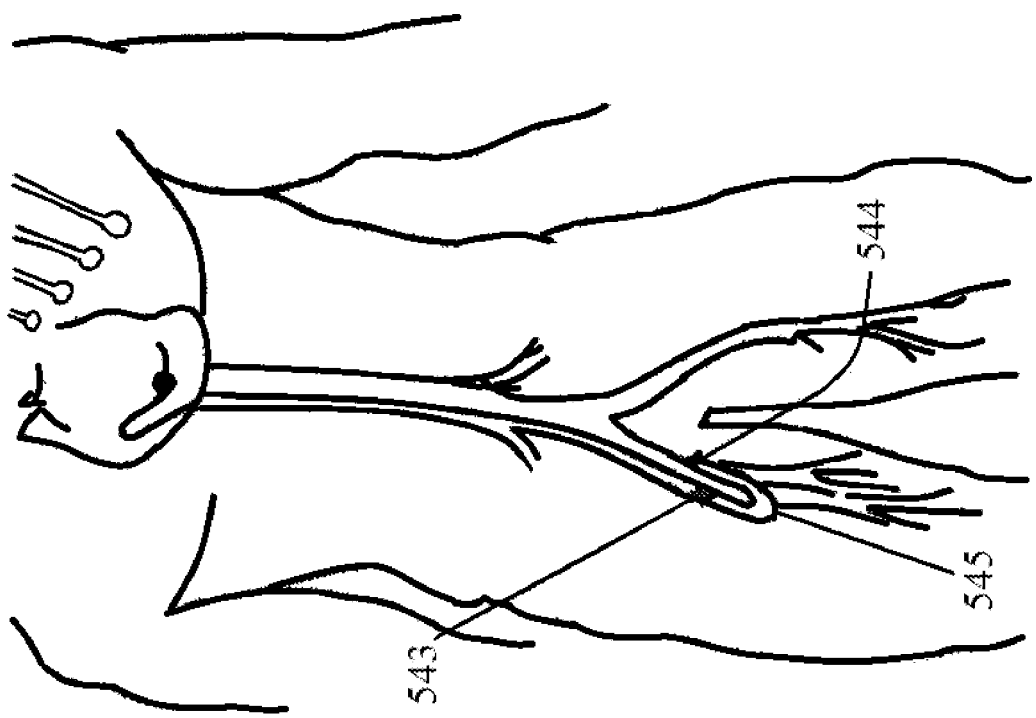
FIG. 5 shows the implantation of the auto-retroperfusion cannulae in the axillary and femoral regions.
Figure 5A:
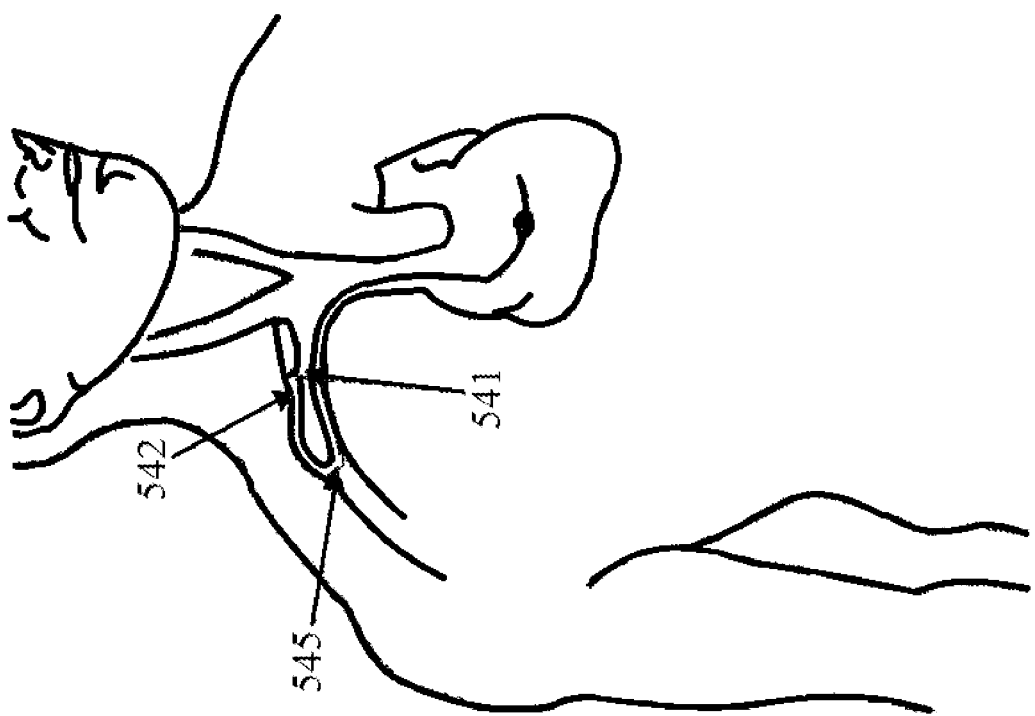

To perform automatic retroperfusion using the present cannula, the axillary vein 441 and the axillary artery 442 are exposed as shown in FIGS. 4A-C and FIG. 5. The same procedure may be performed using the femoral vein 543 and the femoral artery 544 as shown in FIG. 5. The distal end portion of the cannula 400 is then introduced into the axillary vein 441. This may be done using the well-known Seldinger technique, which includes passing the cannula over a guide wire under fluoroscopy. The distal end portion of the cannula is then directed (via fluoroscopy, direct vision, transesophageal echocardiogram, or other suitable means) through the vasculature (e.g., the subclavian vein and the superior vena cava) and into the right atrium of the heart. The distal end portion of the cannula is further advanced through the right atrium and into the coronary sinus 446, which is the coronary vein. When the distal end portion of the cannula reaches the desired location in the coronary sinus, measurement of the sinus is made and the external balloon is inflated accordingly.

Next, an anastomosis 405 of the proximal graft portion 402 of the cannula and the artery 442 may be accomplished by suturing the graft section to the axillary artery as shown in FIG. 4C. This approach could be used for long term arterialization of the coronary venous system, which can replace coronary artery bypass graft.

Alternatively, the autoretroperfusion cannula can be inserted by percutaneous puncture (under local anesthesia) in the axillary vein 541 and axillary artery 542 and both ends connected through a quick connector 545. This procedure may also be performed using the femoral vein 543 and artery 544, as shown in FIG. 5B. This procedure can be used for acute patients or for short periods of arterialization of the coronary veins to stabilize the patient as a bridge to another procedure.

Once the cannula is in place, normal antegrade blood flow continues as usual, but oxygenated blood will be automatically retroperfused through the cannula to the ischemic myocardium via the coronary sinus. The oxygenated blood flow through the cannula occurs throughout the cardiac cycle with a pulsatile flow pattern, but with a peak flow and pressure at the end of systole and the beginning of diastole. Back-flow of blood into the right atrium from the coronary sinus is prevented by the balloon.

It should be noted that the aforementioned procedures can be done under local anesthesia. Depending on the patient's particular condition, auto-retroperfusion can last for minutes, hours, days, or months. During retroperfusion, the secondary lumens can be used for coronary sinus pressure measurement and the delivery of drugs, cells, genes, or growth factors. It is expected that the access ports 406, which are fluidly connected with the secondary lumens, and the graft section will be subcutaneous.

Figure 6B:
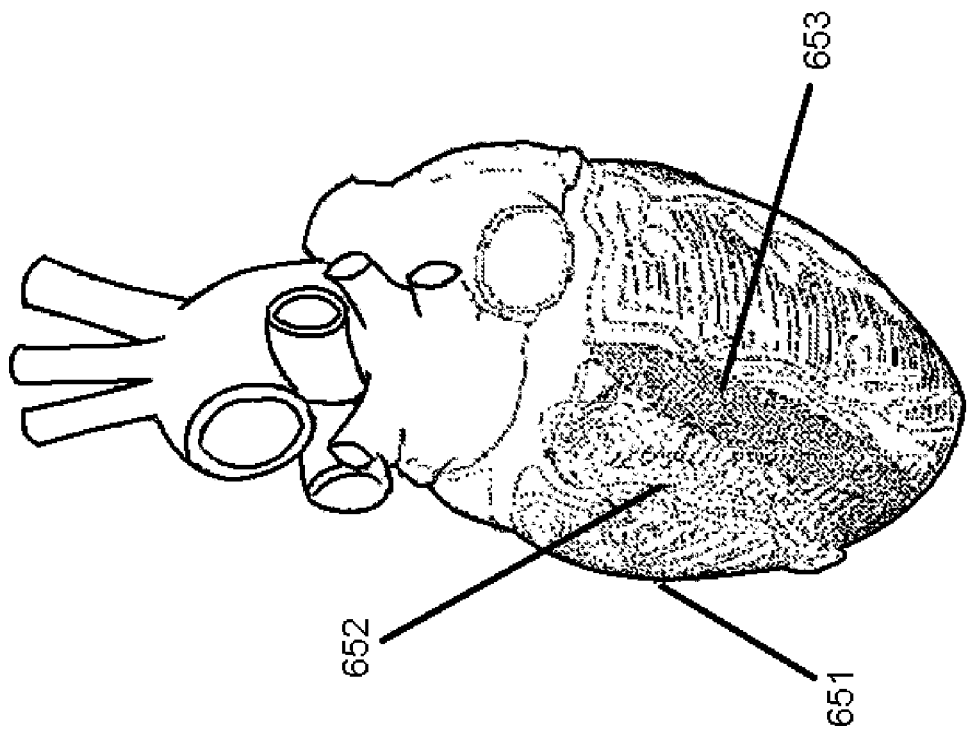
FIG. 6 shows a distribution of selective perfusion territories wherein Zone 1 corresponds to retroperfusion at the level of LAD interventricular anterior vein, which corresponds to the anterior and lateral wall of the left ventricle, and wherein Zone 2 is at the level of the obtuse marginal circumflex vein, and Zone 3 is at the level of the posterolateral circumflex vein.
Figure 6A:
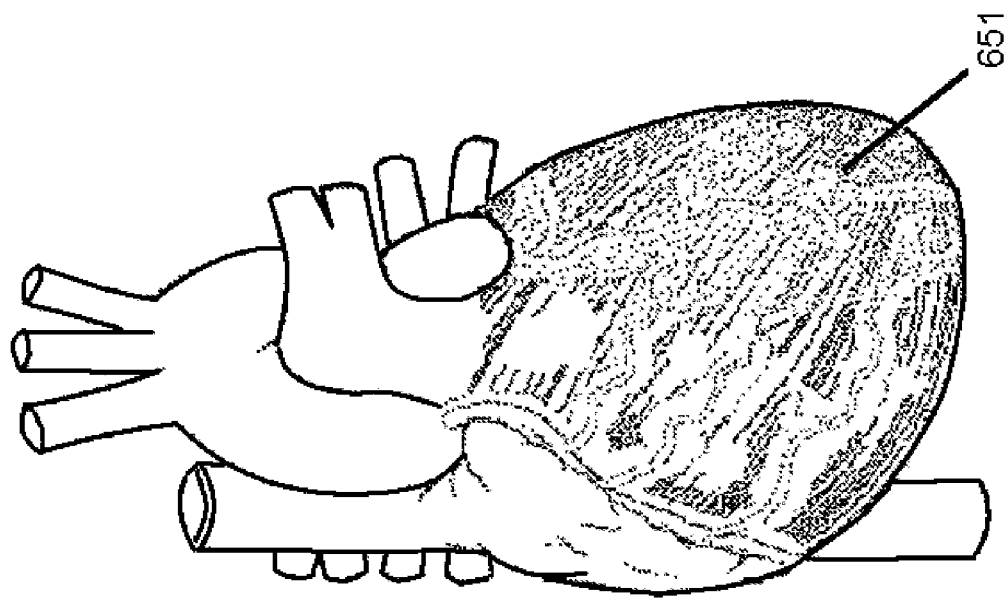

As this method is based on selective retroperfusion, there is a relationship between the site of the coronary sinus where the cannula is anchored and the region of the heart requiring treatment. FIGS. 6A-6B show several zones of interest. Zone 1 651, shown from an anterior view in FIG. 6A and from a posterior view in FIG. 6B, corresponds to retroperfusion at the level of the LAD interventricular anterior vein, which corresponds to the anterior and lateral wall of the left ventricle. This is the largest area of the left ventricle to be perfused and hence clinically the most relevant. This area is the most distal to the coronary sinus and can be determined by sizing of the vein through the impedance electrodes. Zone 2 652 covers the level of the obtuse marginal circumflex vein and is more proximal to the coronary sinus. Zone 3 653 covers the level of the posterolateral circumflex vein, which is the smallest area of the left ventricle to be perfused and is the most proximal to the coronary sinus. Hence, the position of the catheter, which can be determined by sizing of the vein through impedance measurements, can determine the perfusion territory. This will serve as a clinical strategy to treat patients with LAD or LCx disease.

In addition to the foregoing, and in various embodiments of devices (such as cannulas 100, 200, and 400 and/or grafts 302, for example, of the present disclosure, such cannulas 100, 200, and 400 and/or grafts 302 may optionally comprise a regional hypothermia system 4000 configured in accordance with the following. Various regional hypothermia systems 4000 of the present disclosure, as shown in component block diagram of FIG. 7 and as referenced in further detail herein, are configured for use to cool (reduce the temperature of) blood and/or other fluids within the body for targeted delivery to a location within the body. Such cooling can be from, for example, at or about 0.5° C. to as much as 10° C. cooler, for example, than the native temperature of blood within the mammalian body. In some embodiments, localized blood cooling of greater than 10° C. may be desired and accomplished using one or more regional hypothermia systems 4000 of the present disclosure.

In various embodiments, regional hypothermia systems 4000 are configured for use within a mammalian body even at tissues that are relatively difficult to reach due to, for example, potential occlusion of one or more coronary and/or cerebral arteries. Such regional hypothermia systems 4000 of the present disclosure may be useful in connection with the reduction of perfusion injuries by cooling the region of risk, whether it be at, near, or in the heart and/or brain, may be critical to reduce reperfusion injury and to decrease infarct size, for example, prior to opening an artery in the heart or brain. Retroperfusion, as referenced generally herein, provides an ideal mechanism to deliver blood at a target location, and the use of a regional hypothermia system 4000 of the present disclosure in connection with one or more cannulas 100, 200, and 400 and/or grafts 302 of the present disclosure can effectively deliver blood at a desired/targeted temperature by way of delivery through open veins, for example, to the region at risk, such as a heart or brain. In general, such cannulas 100, 200, and 400 and/or grafts 302, in connection with the use of one or more regional hypothermia systems 4000 of the present disclosure, can allow perfusion/retroperfusion of oxygenated blood, control blood perfusion pressure within a vessel, condition a blood vessel to operate under higher blood pressure (such as arterialization of a vein), increase flow of oxygenated blood to ischemic myocardium, and/or decrease the acute ischemic area during a myocardial infarct event, all at a relatively colder temperature than would otherwise be allowed without the use of a regional hypothermia system.

Figure 7:
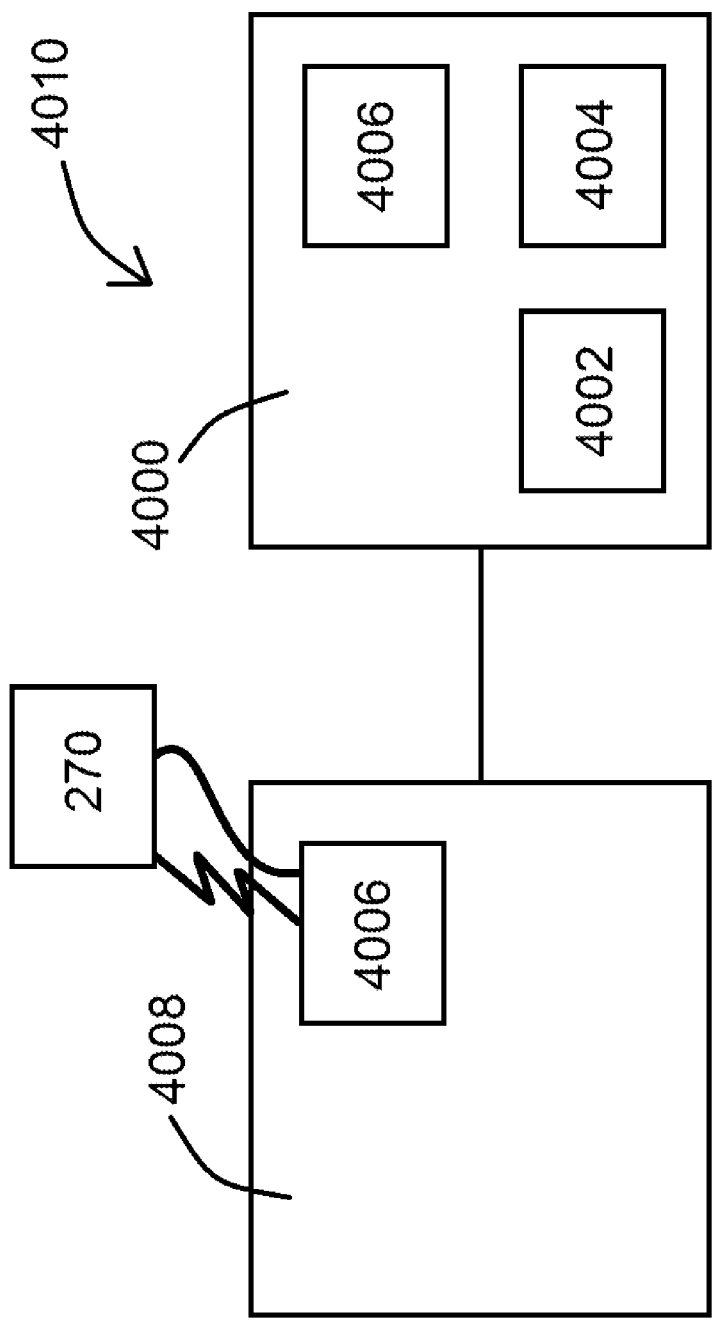
FIG. 7 shows a block diagram of a regional hypothermia system and kit used in connection with an exemplary device or system of the present disclosure.

In at least one embodiment of a regional hypothermia system 4000 of the present disclosure, and as shown in FIG. 7, regional hypothermia system 4000 comprises a heat exchanger 4002 coupled to one or more components of cannulas 100, 200, and 400 and/or grafts 302 of the present disclosure. Heat exchanger 4002, in various embodiments, is configured to reduce the temperature of blood passing through one or more components of cannulas 100, 200, and 400 and/or grafts 302, so that the blood that is ultimately delivered to the targeted area of interest, such as being at, near, or in the heart and/or brain or at or near another tissue or targeted blood vessel, is at a lower temperature than normal (or without the use of a regional hypothermia system 4000). For example, and in at least one embodiment, regional hypothermia system 4000 is used to reduce the temperature of blood delivered at, near, or in the heart and/or brain by or about 3° C. to 4° C. via the general blood circuit created using various cannulas 100, 200, and 400 and/or grafts 302.

Heat exchanger 4002, as referenced herein, can utilize one or more cooling products 4004, such as perfluorocarbon, liquid carbon dioxide, helium, another cooled gas, and/or another refrigerant or refrigeration mechanism known in the art, that facilitates the cooling of blood, and ultimately tissues at or near the cooled blood, through components of cannulas 100, 200, and 400 and/or grafts 302 of the present disclosure. Furthermore, one or more temperature sensors 4006 can be coupled to various components of cannulas 100, 200, and 400 and/or grafts 302 of the present disclosure, so that blood and/or tissue temperature(s) (including temperatures at, near, or in the heart and/or brain or other tissues or blood vessels, depending on the type of cannulas 100, 200, and 400 and/or grafts 302 used) can be detected by temperature sensors 4006 and transmitted (via wire or wirelessly) to a remote module 270 and/or another data acquisition and processing system/mechanism so that a user of regional hypothermia system 4000 can regulate localized temperature (at, near, or in the heart or brain or other tissues or blood vessels, for example), as desired. A generic device 4008 is shown in FIG. 7 as being operably coupled to an exemplary regional hypothermia system 4000 of the present disclosure, whereby generic device 4008 may comprise one or more cannulas 100, 200, and 400 and/or grafts 302, other devices and/or systems of the present disclosure, and/or individual components thereof. An exemplary kit 4010 of the present disclosure, as shown in the figures, comprises an exemplary regional hypothermia system 4000 operably coupled to an exemplary generic device 4008 of the present disclosure.

Further, and in various embodiments, heat exchanger 4004 can be at the level of an arterial-venous connector, a double-lumen catheter, and/or another component of one or more cannulas 100, 200, and 400 and/or grafts 302 of the present disclosure. For the heart, this can be particularly important for patients with a door-to-balloon time of greater than two hours, for patients with ST segment elevation myocardial infarction (STEMI) that are at high risk for reperfusion injury, and/or patients with hemodynamics instability. There are several advantages to using a regional hypothermia system 4000 of the present disclosure, including but not limited to rapid percutaneous insertion and rapid cooling of the myocardial area before opening the culprit artery to avoid the cascade of inflammatory reactions responsible for reperfusion injury.

As referenced generally above, various regional hypothermia systems 4000 of the present disclosure are configured and operable to introduce mild hypothermia to reduce cardiac infarct size and general severity of the same. Such systems 4000, in connection with various cannulas 100, 200, and 400 and/or grafts 302 of the present disclosure, can treat chronic and acute heart failure, as needed, and generally reduce the severity of an injury and/or reduce inflammation as referenced herein, by way of regionally reducing blood temperature.

While various embodiments of devices for controlling blood perfusion along with regional mild hypothermia and methods of using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A perfusion device, comprising:
    an elongated body having a lumen, a proximal end configured for placement in a first area having a first blood pressure, and a distal end configured for placement in a second area having a second blood pressure;
    a partial occluder positioned within the lumen of the elongated body that does not fully occlude the lumen, the partial occluder disposed within the elongated body, the partial occluder configured to reduce in size over time so that when the partial occluder reduces in size over time, blood flow through the lumen at the partial occluder can increase over time, the partial occluder forming a narrowed lumen concentric with the lumen of the elongate body;
    wherein the lumen comprises only one opening proximal the partial occluder; and
    a regional hypothermia system operably coupled thereto, the regional hypothermia system operable to reduce and/or regulate a temperature of a bodily fluid flowing therethrough.

2. The device of claim 1, wherein the regional hypothermia system is further operable to reduce and/or regulate a temperature of a portion of a mammalian body, the portion selected from the group consisting of a vessel, a tissue, and an organ.

3. The device of claim 1, wherein the regional hypothermia system comprises a heat exchanger configured to reduce and/or regulate the temperature of the bodily fluid.

4. The device of claim 1, wherein one or more components of the regional hypothermia system uses a cooling product to reduce and/or regulate the temperature of the bodily fluid.

5. The device of claim 1, further comprising:
    one or more temperature sensors coupled to the device, the one or more temperature sensors operable to detect the temperature of the bodily fluid.

6. The device of claim 5, wherein the regional hypothermia system further comprises a remote module in wired or wireless communication with the one or more temperature sensors, the remote module operable to and configured to receive the detected temperature(s) and process the same to regulate, reduce, and/or increase the temperature of the bodily fluid by way of altering an operation of the regional hypothermia system.

7. The device of claim 1, wherein the partial occluder comprises a resorbable stenosis, wherein the resorbable stenosis is configured to be resorbed over time when contacted by blood flowing through the lumen of the elongated body.

8. The device of claim 1, wherein the partial occluder comprises:
an occlusion balloon configured to deflate in size from a first size to a second size, the second size comprising a deflated state or the absence of occlusion of the lumen after a period of time.

9. The device of claim 1, wherein the elongated body further comprises:
an anchoring balloon configured to anchor the elongated body within part of a circulatory system.

10. A method, comprising the steps of:
introducing a distal end of an elongated tubular body of a perfusion device into a blood vessel to be conditioned, the blood vessel having a first blood pressure therein, the perfusion device comprising:
the elongated body having a lumen, a proximal end configured for placement in a first area having the first blood pressure, and the distal end configured for placement in a second area having a second blood pressure,
a partial occluder positioned within the lumen of the elongated body that does not fully occlude the lumen, the partial occluder disposed within the elongated body, the partial occluder configured to reduce in size over time so that when the partial occluder reduces in size over time, blood flow through the lumen at the partial occluder can increase over time, the partial occluder forming a narrowed lumen concentric with the lumen of the elongate body,
wherein the lumen comprises only one opening proximal the partial occluder, and
a regional hypothermia system operably coupled thereto, the regional hypothermia system operable to reduce and/or regulate a temperature of a bodily fluid flowing therethrough;
introducing the proximal end of the elongated tubular body into a second blood vessel such that blood flow is received within the interior of the elongated tubular body, the second blood vessel having a second blood pressure therein which is higher than the first blood pressure;
reducing and/or regulating a temperature of blood flowing through the elongated tubular body using the regional hypothermia system operably coupled to the elongated tubular body; and
reducing the size of the stenosis over time such that the first blood pressure at the distal end of the elongated body is approximately the same as the second blood pressure at the proximal end.

11. The method of claim 10, wherein the elongated tubular body introduced into the blood vessel and the second blood vessel further comprises an anchoring balloon configured to anchor the elongated tubular body within part of a circulatory system, and wherein the method further comprises the step of:
inflating the anchoring balloon to anchor the elongated tubular body within the blood vessel or the second blood vessel.

12. The method of claim 10, wherein the stenosis comprises a balloon occlusion and the step of reducing the height of the stenosis over time comprises deflating or removing the balloon occlusion positioned within the interior of the elongated tubular body.

13. The method of claim 10, wherein the stenosis comprises a resorbable stenosis and the step of reducing the height of the stenosis over time comprises deflating the gradual resorption of the stenosis within the interior of the elongated tubular body.

14. The method of claim 10, wherein the step of reducing and/or regulating a temperature of blood flowing through the elongated tubular body is performed to treat a cardiac condition.

15. A cannula, comprising:
an elongated body having a lumen, a proximal end configured for placement in a first area having a first blood pressure, a distal end configured for placement in a second area having a second blood pressure, wherein the first blood pressure is higher than the second blood pressure;
a partial occluder positioned within the lumen of the elongated body between the proximal end and the distal end and closer to the proximal end than the distal end, the partial occluder disposed within the elongated body, the partial occluder selected from the group consisting of an occluder balloon and a resorbable stenosis, the partial occluder configured so, at a initial height thereof, the partial occluder does not fully occlude the lumen of the elongated body and further configured to gradually equalize the first blood pressure at the first area with the second blood pressure at the second area, the partial occluder forming a narrowed lumen concentric with the lumen of the elongate body;
wherein the lumen comprises only one opening proximal the partial occluder; and
a regional hypothermia system operably coupled thereto, the regional hypothermia system operable to reduce and/or regulate a temperature of a bodily fluid flowing therethrough.

16. The cannula of claim 15, wherein the regional hypothermia system is further operable to reduce and/or regulate a temperature of a portion of a mammalian body, the portion selected from the group consisting of a vessel, a tissue, and an organ.

17. The cannula of claim 15, wherein the regional hypothermia system comprises a heat exchanger configured to reduce and/or regulate the temperature of the bodily fluid, and wherein the cannula further comprises one or more temperature sensors coupled thereto, the one or more temperature sensors operable to detect the temperature of the bodily fluid.

18. The cannula of claim 15, wherein the elongated body further comprises:
an anchoring balloon configured to anchor the elongated body within part of a circulatory system.

19. The cannula of claim 15, wherein the partial occluder comprises the resorbable stenosis, wherein the resorbable stenosis is configured to be resorbed over time when contacted by blood flowing from the proximal end to the distal end of the elongated body.

20. The cannula of claim 15, wherein the partial occluder comprises the occlusion balloon, wherein the occlusion balloon is configured for inflation to partially occlude the lumen when in an inflated state and further configured for deflation or removal after a period of time.

* * * * *